US009664734B2

(12) United States Patent
Malkova et al.

(10) Patent No.: US 9,664,734 B2
(45) Date of Patent: May 30, 2017

(54) MULTI-OSCILLATOR, CONTINUOUS CODY-LORENTZ MODEL OF OPTICAL DISPERSION

(71) Applicant: KLA-Tencor Corporation, Milpitas, CA (US)

(72) Inventors: Natalia Malkova, Hayward, CA (US); Leonid Poslavsky, Belmont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/158,883

(22) Filed: May 19, 2016

(65) Prior Publication Data

US 2016/0341792 A1   Nov. 24, 2016

Related U.S. Application Data

(60) Provisional application No. 62/165,021, filed on May 21, 2015.

(51) Int. Cl.
*G01B 11/02* (2006.01)
*G01B 7/02* (2006.01)
(Continued)

(52) U.S. Cl.
CPC ......... *G01R 31/308* (2013.01); *G01N 21/211* (2013.01); *G01N 21/8422* (2013.01);
(Continued)

(58) Field of Classification Search
CPC ............... G01N 21/41; G01N 21/9501; G01N 21/8851; G01N 21/8422; G01N 21/211;
(Continued)

(56) References Cited

U.S. PATENT DOCUMENTS 6,465,265 B2   10/2002   Opsal et al.
7,239,391 B2   7/2007   Synowicki et al.
(Continued)

OTHER PUBLICATIONS

Cody, G. D., et al., "Effect of site disorder on the Optical absorption edge of a-Si:Hx" J. of Non-Crystal. Solids 59, 3, 60 325-328 (1983).
(Continued)

*Primary Examiner* — Kimberly Rizkallah
*Assistant Examiner* — Brian Turner
(74) *Attorney, Agent, or Firm* — Spano Law Group; Joseph S. Spano

(57) ABSTRACT

Methods and systems for monitoring band structure characteristics and predicting electrical characteristics of a sample early in a semiconductor manufacturing process flow are presented herein. High throughput spectrometers generate spectral response data from semiconductor wafers. In one example, the measured optical dispersion is characterized by a Gaussian oscillator, continuous Cody-Lorentz model. The measurement results are used to monitor band structure characteristics, including band gap and defects such as charge trapping centers, exciton states, and phonon modes in high-K dielectric layers and embedded nanostructures. The Gaussian oscillator, continuous Cody-Lorentz model can be generalized to include any number of defect levels. In addition, the shapes of absorption defect peaks may be represented by Lorentz functions, Gaussian functions, or both. These models quickly and accurately represent experimental results in a physically meaningful manner. The model parameter values can be subsequently used to gain insight and control over a manufacturing process.

20 Claims, 3 Drawing Sheets

(51) Int. Cl.
  *G01N 21/21* (2006.01)
  *G01N 21/95* (2006.01)
  *H01L 21/36* (2006.01)
  *H01L 21/66* (2006.01)
  *G01R 31/308* (2006.01)
  *G01N 21/84* (2006.01)

(52) U.S. Cl.
  CPC ......... *G01N 21/9501* (2013.01); *H01L 22/12* (2013.01); *H01L 22/20* (2013.01); *G01N 2021/213* (2013.01); *G01N 2201/12* (2013.01)

(58) Field of Classification Search
  CPC ... G01B 11/0625; G01R 31/308; H01L 22/12; H01L 22/20
  USPC ......... 257/607; 356/237.5, 369, 504; 438/10
  See application file for complete search history.

(56) References Cited

U.S. PATENT DOCUMENTS

| | | | |
|---|---|---|---|
| 7,414,721 | B1 | 8/2008 | Suvkhanov et al. |
| 8,711,349 | B2 | 4/2014 | Gao et al. |
| 2004/0257567 | A1* | 12/2004 | Woollam ............. G01N 21/211 356/369 |
| 2010/0068834 | A1 | 3/2010 | Hachigo et al. |
| 2013/0083320 | A1 | 4/2013 | Gao et al. |

OTHER PUBLICATIONS

Cody, G. D., et al., "Disorder and Optical-Absorption edge of Hydrogenated Amorphous Silicon" Phys. Rev. Lett. 17, 1480-1483 (1981).

MacDonald, S.A. et al., "Dispersion analysis of FTIR reflection measurements in silicate glasses," J. of Non-Crystalline Solids 275, 72-82 (2000).

Ferlauto, A.S., et al., "Analytical Model for the optical function of an amorphous semiconductor from the near-infrared to ultraviolet: Application in thin film photovoltaics," J. Appl. Phys. 92, 2424 (2002).

Di, M., et al., "Comparison of methods to determine bandgaps of ultrathin HfO2 films using spectroscopic ellipsometry," J. Vac. Sci. Technol. A 29, 041001 (2011).

Meneses, D.D.S. et al., "Structure and lattice dynamics of binary silicate glasses investigated by infrared spectroscopy," J. of Non-Crystalline Solids 352, 769-776 (2006).

Nguyen, N.V. et al., "Sub-bandgap defect states in polycrystalline hafnium oxide and their suppression by admixture of silicon," APL 87, 192903 (2005).

Nguyen, N.V. et al., "Optical properties of Jet-Vapor-Deposited TiAlO and HfAlO determined by Vacuum Ultraviolet Spectroscopic Ellipsometry," AIP Conf. Proc. 683, 181 (2003).

International Search Report mailed on Aug. 23, 2016, for PCT Application No. PCT/US2016/033613 filed on May 20, 2016 by KLA-Tencor Corporation, 6 pages.

Orava, J. et al., "Optical properties and phase change transition in Ge2SbsTe5 flash evaporated thin films studied by temperature dependent spectroscopic ellipsometry" J of Applied Physics,vol. 104, No. 4, Aug. 27, 2008.

Budai, Judit et al., "Ellipsometric study of SiC films: Analysis of Tauc Lorentz and Gaussian oscillator models" Thin Solid Films, vol. 519, No. 9, Feb. 2011.

Qiying, Liang, et al. "Convenient and inexpensive determination of optical constants and film thickness of blended organic thin film" Science China Physics, Mechanics & Astonomy, Science China Press, Jul. 2014.

Falahatgar, S S et al. "A developed model for the determination of the dielectric function for some absorbing thin films using pseudo-Urbach tail". Physica B. Condensed Matter, Dec. 2012.

He, G., et al., "Thickness-modulated Optical Dielectric Constants and Band Alignments of HfOxNy Gate Dielectrics," Journal of Applied Physics, Jan. 14, 2009, 105, 014109, pp. 1-4, USA.

Price, J., et al., "Identification of Interfacial Defects in High-k Gate Stack Films by Spectroscopic Ellipsometry," Journal of Vacuum Science and Technology, American Vacuum Society, Feb. 9, 2009, B 27(1), pp. 310-312, USA.

Price, J., et al., "Identification of Sub-Band-Gap Absorption Features At the HfO2/Si(100) Interface Via Spectroscopic Ellipsometry," Applied Physics Letters, American Institute of Physics, Aug. 10, 2007, 91, 061925, pp. 1-3, USA.

Cody, G.D., "The Optical Absorption Edge of a Si:H," Semiconductors and Semimetals 21, 11 (1984).

* cited by examiner

MULTI-OSCILLATOR, CONTINUOUS CODY-LORENTZ MODEL OF OPTICAL DISPERSION

CROSS REFERENCE TO RELATED APPLICATION

The present application for patent claims priority under 35 U.S.C. §119 from U.S. provisional patent application Ser. No. 62/165,021, entitled "New Multi-Oscillator Cody-Lorentz-Continuous-Lorentz-Gaussian Model for Tracking of Bandgap, Structure and/or Electronic Defects, Excitonic States, and Phonon Modes in New Technological Important Materials," filed May 21, 2015, the subject matter of which is incorporated herein by reference.

TECHNICAL FIELD

The described embodiments relate to systems for optical characterization of structures and materials employed in semiconductor manufacturing.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

Semiconductor devices are increasingly valued based on their energy efficiency, rather than speed alone. For example, energy efficient consumer products are more valuable because they operate at lower temperatures and for longer periods of time on a fixed battery power supply. In another example, energy efficient data servers are in demand to reduce their operating costs. As a result, there is a strong interest to reduce the energy consumption of semiconductor devices.

Leakage current through insulator layers is a major energy loss mechanism of semiconductor devices manufactured at the 65 nm technology node and below. In response, electronic designers and manufacturers are adopting new materials (e.g., hafnium silicate ($HfSiO_4$), nitrided hafnium silicates (HfSiON), hafnium dioxide ($HfO_2$), zirconium silicate ($ZrSiO_4$), etc.) with higher dielectric constants than traditional materials (e.g., silicon dioxide). These "high-k" materials reduce leakage current and enable the manufacture of smaller sized transistors.

Along with the adoption of new dielectric materials, the need has arisen for measurement tools to characterize the dielectric properties and band structures of high-k materials early in the manufacturing process. More specifically, high throughput monitoring tools are required to monitor and control the deposition of high-k materials during wafer manufacture to ensure a high yield of finished wafers. Early detection of deposition problems is important because the deposition of high-k materials is an early process step of a lengthy and expensive manufacturing process. In some examples, a high-k material is deposited on a wafer at the beginning of a manufacturing process that takes over one month to complete.

The performance of a logic gate is commonly characterized in terms of electrical characteristics such as equivalent oxide thickness (EOT), leakage current, threshold voltage, leakage EOT, and breakdown voltage. During device processing it is important to monitor and control these parameters. These electrical characteristics may be studied by a variety of methods including electrical measurements, transmission electron microscopy, x-ray spectroscopy and scattering, atomic force microscopy, and photoelectronic spectroscopy. Currently, however, these measurement technologies suffer from any of a number of limitations. In some cases, the measurements require destruction of the sample. In some cases, many post-deposition processing steps must be completed before measurements can occur. In some cases, the measurement technology is slow, and must be separated from the production line.

Optical metrology tools offer the possibility of high throughput, in-line, non-destructive characterization of electrical characteristics of device materials and structures, such as gate structures. In particular, the spectroscopic ellisometry (SE) measurement technique includes a parametric representation of a measured optical dispersion. In some examples, the parameterized model represents a dielectric function having a direct relation to the band gap of the device constituents as well as their structure/electrical defects; all major factors determining device electrical performance. In general, the particular parameterization is selected to reduce the number of unknown parameters and decrease correlations among parameters.

In some examples, the optical response of one or more high-K dielectric layers is predicted based on a direct inversion method. These methods are described by way of example in J. Price et al., "Identification of interfacial defects in high-k gate stack films by spectroscopic ellipsometry," J. Vac. Sci. Technol. B 27 (1), 310 (2009) and J. Price et al., "Identification of sub-band-gap absorption features at the $HfO_2$/Si(100) interface via spectroscopic ellipsometry," APL 91, 061925 (2007), the subject matter of each is incorporated herein by reference in their entirety. However, direct inversion methods are computationally burdensome, very sensitive to statistical measurement errors, and do not provide a physically based model of the measured structure (i.e., the optical functions do not satisfy the Kramers-Kronig consistency condition). As a result, the utility of direct inversion methods for high-throughput inspection and process control is limited for in-line measurement applications. In addition, the direct inversion method involves an ill-defined mathematical problem. SE measurements provide two values (e.g., $\alpha$ and $\beta$, $\Psi$ and $\Delta$, etc.) for each measured wavelength, but the model inversion must generate estimates for three unknowns. For example, the inversion might provide estimates for the real ($\in_1$) and imaginary ($\in_2$) parts of the dielectric function and film thickness. In another example, the inversion might provide estimates for the refractive index (n) and extinction coefficient (k) and film thickness. The solution to this ill-defined problem requires the introduction of artificial, simplifying assumptions that introduce undesirable errors. As a result the optical functions delivered by the direct inversion method lack physical meaning.

In some other examples, the optical response of one or more high-K dielectric layers is predicted based on a Bruggeman Effective Model Approximation (BEMA) model. The BEMA model represents the dielectric function of the layer as an effective composition of assumed dielectric functions of constituents. The optimized effective composition is then related to the composition of the dielectric layer of interest. In general, the BEMA model is based on Kramers-Kronig consistent dielectric functions of constituents, and thus is itself Kramers-Kronig consistent. As a result, the BEMA model yields physically reasonable results. However, the value of the band gap as derived from the BEMA model is an indirect measurement that requires a reference to provide meaningfully accurate results.

Both the BEMA and the direct inversion method are used to extract dispersion curves (e.g., the real ($\in_1$) and the imaginary ($\in_2$) parts of the dielectric function, or refractive index (n) and extinction coefficient (k)) from SE measurements. Subsequently, the calculated dispersion curves must be interpolated in the energy range of interest to evaluate the band gap. The accuracy of the band gap estimate depends strongly on the choice of the energy of interest for band gap interpolation. Moreover, since band gap must be indirectly derived from the calculated dispersion curves, a reference is required to provide accurate results. For these practical reasons, both BEMA and direct inversion are limited in their ability to accurately monitor band gap.

In some other examples, a Tauc-Lorentz model or a Cody-Lorentz model is employed as described by way of example in A. S. Ferlauto et al., "Analytical model for the optical functions of amorphous semiconductors from the near-infrared to ultraviolet: Application in thin film photovoltaics," J. Appl. Phys. 92, 2424 (2002), the subject matter of which is incorporated herein by reference in its entirety. In these models, the imaginary part of the dielectric function is represented by a parameterized dispersion function, and the real part of the dielectric function is determined based on enforcement of Kramers-Kronig consistency. Model parameters (e.g., optical function parameters and thicknesses) are evaluated by fitting modeled spectra to measured spectra by numerical regression. The validity and limitations of the models are assessed by statistical evaluation of fitting quality and confidence limits of model parameters.

Although Tauc-Lorenz and Cody-Lorentz models may be successfully applied to the characterization of defect free semiconductor and dielectric films, band gap values as well as defect states are evident in optical and transport measurements of practical dielectric and semiconductor layers. Thus, optical functions employed in SE measurements must include band gap and defect states to be effective for process monitoring. Unfortunately, the Tauc-Lorentz and Cody-Lorentz models intrinsically fail to represent such states. In one example, the sum of three Tauc-Lorentz functions is used to describe near band-edge defects in HfO2 layers, as described by N. V. Nguyen et al., "Sub-bandgap defect states in polycrystalline hafnium oxide and their suppression by admixture of silicon," APL 87, 192903 (2005); and N. V. Nguyen et al., "Optical properties of Jet-Vapor-Deposited TiAlO and HfAlO determined by Vacuum Ultraviolet Spectroscopic Ellipsometry," AIP Conf. Proc. 683, 181 (2003), the subject matter of each is incorporated herein by reference in their entirety. However, these functions fail to describe sharp middle gap peaks noticeable in the absorption spectra of high-K stacks. Moreover, the Tauc-Lorentz model is unable to account for low energy absorption tails characteristic of amorphous materials.

Although, in principle, a Harmonic Oscillator model may be employed to represent defect states, there is an indirect connection between model parameters and meaningful physical values (e.g., defect activation energy, number of defects, etc.). Thus, a Harmonic Oscillator model has not proven feasible for the characterization of defect states.

Accordingly, it would be advantageous to develop high throughput systems and methods for characterizing structures and materials early in the manufacturing process. In particular, it would be advantageous to develop a robust, reliable, and stable approach to in-line SE metrology of gate stacks including high-K dielectrics.

SUMMARY

Methods and systems for monitoring bandgap, defect states, and other material parameters to predict electrical characteristics of a sample early in a production flow are presented herein. More specifically, optical models of structures and materials employed in semiconductor device manufacture based on a Gaussian Oscillator, Continuous-Cody-Lorentz (GOCCL) model are presented. In particular, models capable of accurate characterization of band structure characteristics in high-K dielectric layers and nanostructures such as quantum wells, quantum dots and nanowires embedded in another amorphous dielectric slab or layer are presented. Measured band structure characteristics include bandgap, defect states, interface states, excitonic effects, etc. These models quickly and accurately represent experimental results in a physically meaningful manner that can be subsequently used to gain insight and control over a manufacturing process. The optical models presented herein are employed to represent structures incorporating a variety of new, technologically important materials. The measurement results are used to control band gap and defects such as charge trapping centers, exciton states, and phonon modes.

In one aspect, the selected dispersion model includes a Gaussian oscillator, continuous Cody-Lorentz model. The Gaussian oscillator, continuous Cody-Lorentz model can be generalized to include any number of the defect levels. In addition, the shapes of absorption defect peaks may be represented by Lorentz functions, Gaussian functions, or both. Gaussian functions enable improved representation of a variety of physical features of measured structures including excitonic and chaos effects.

In a further aspect, a band structure characteristic indicative of an electrical performance of the measured layer, or stack of layers, is determined based at least in part on the parameter values of the optical dispersion model of the multi-layer semiconductor wafer. In some embodiments, the optical band gap is determined based at least in part on the parameter values of the optical dispersion model of the multi-layer semiconductor wafer. Moreover, the electrical performance of unfinished semiconductor devices is accurately predicted based on accurate estimates of the optical band gap derived from measurements of the target layer, or stack of layers, and the measurement models described herein.

In another further aspect, device performance is improved by controlling a process of manufacture of the semiconductor wafer based at least in part on the identified band structure characteristic. In one example, layer thickness may be controlled based on band gap characteristics identified from the parameter values of the optical dispersion model.

The foregoing is a summary and thus contains, by necessity, simplifications, generalizations, and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for monitoring bandgap, defect states, and other material parameters to predict electrical characteristics of a sample early in a production flow are presented herein.

More specifically, optical models of structures and materials employed in semiconductor device manufacture based on a Gaussian Oscillator, Continuous-Cody-Lorentz (GOCCL) model are presented. In particular, models capable of accurate characterization of band structure characteristics in high-K dielectric layers, defect states, interface states, excitonic effects and nanostructures such as quantum wells, quantum dots and nanowires embedded in another amorphous dielectric slab or layer are presented. These models quickly and accurately represent experimental results in a physically meaningful manner. The results are subsequently used to gain insight and control over a manufacturing process. The optical models presented herein are employed to represent structures incorporating a variety of new, technologically important materials. The measurement results are used to control band gap and defects such as charge trapping centers, exciton states, and phonon modes.

Figure 1:
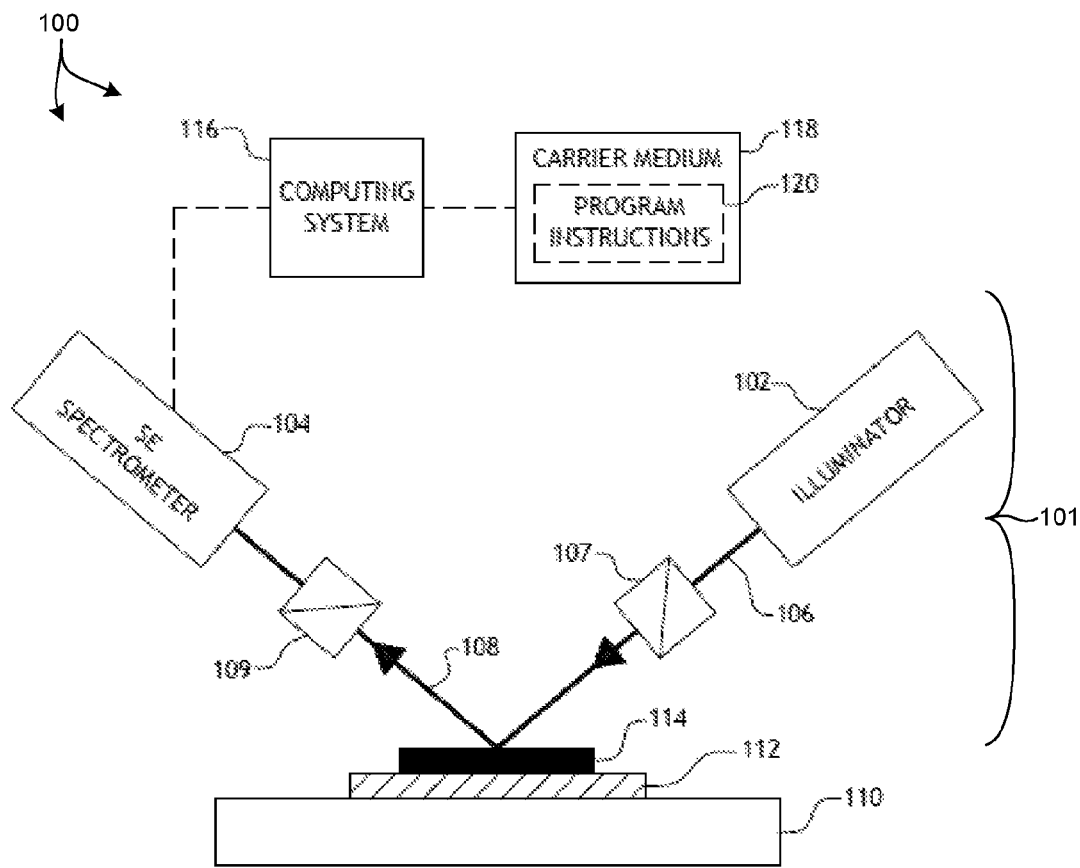
FIG. 1 is a simplified diagram illustrative of a wafer inspection system 100 including thin film characterization functionality.

FIG. 1 illustrates a system 100 for measuring a spectral response of a thin film of a semiconductor wafer, in accordance with one embodiment of the present invention. As shown in FIG. 1, the system 100 may be used to perform spectroscopic ellipsometry on one or more films 114 of a semiconductor wafer 112 disposed on a translation stage 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-850 nm) to the thin film (e.g., HfSiON thin film) disposed on the surface of the semiconductor wafer 112. In turn, the spectrometer 104 is configured to receive illumination reflected from the surface of the semiconductor wafer 112. It is further noted that the light emerging from the illuminator 102 is polarized using polarizer 107 to produce a polarized illumination beam 106. The radiation reflected by the thin film 114 disposed on the wafer 112 is passed through an analyzer 109 and to the spectrometer 104. In this regard, the radiation received by the spectrometer 104 in the collection beam 108 is compared to the incident radiation of the illumination beam 106, allowing for spectral analysis of the thin film 114.

In a further embodiment, the system 100 may include one or more computing systems 116. The one or more computing systems 116 may be communicatively coupled to the spectrometer 104. In one aspect, the one or more computing systems 116 may be configured to receive a set of spectral measurements performed by the spectrometer 104 on one or more wafers. Upon receiving results of the one or more sampling process from the spectrometer, the one or more computing systems 116 may then calculate parameters of an optical dispersion model. In this regard, the computing system 116 may extract the real component (n) and the imaginary component (k) of the complex index of refraction of the thin film across the selected spectral range (e.g., 150-850 nm) for the acquired spectrum from the spectrometer 104. Further, the computing system 116 may extract the n- and k-curves utilizing a regression process (e.g., ordinary least squares regression) applied to a selected dispersion model. In a preferred embodiment, the selected dispersion model is a Gaussian Oscillator, Continuous-Cody-Lorentz model as described herein.

In a further embodiment, the computing system 116 may determine a band structure characteristic indicative of a defect of the film 114 based on parameter values of the optical dispersion model. For example, the computing system 116 may be configured to automatically identify defects from parameter values of the optical dispersion model.

In another further embodiment, the computing system 116 may control a process of manufacture a semiconductor wafer based at least in part on a band structure characteristic determined from parameter values of the optical dispersion model. For example, computing system 116 may be configured to communicate process control parameter values to one or more manufacturing tools responsible for the manufacture of the semiconductor wafers being measured.

Figure 2:
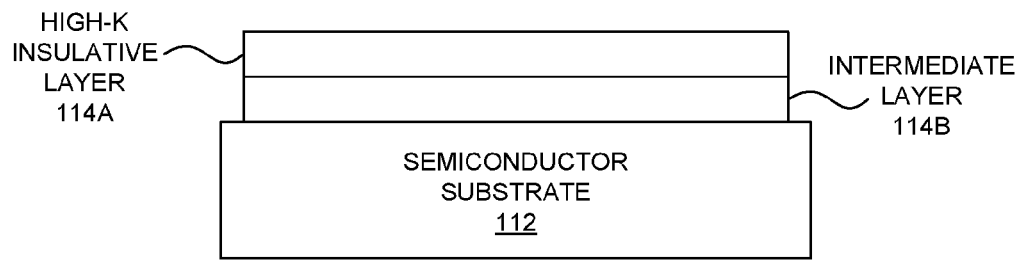
FIG. 2 is a simplified diagram illustrative of a semiconductor substrate 112 with attached thin film layers 114A and 114B that may be characterized by methods and systems as described herein.

As illustrated in FIG. 2, in some embodiments, an intermediate layer 114B is located between a semiconductor substrate 112 (e.g., silicon) and a high-k insulative layer 114A to promote adhesion between the high-k material and the semiconductor substrate. Typically, the intermediate layer 114B is very thin (e.g., ten Angstroms). In some examples, the high-k insulative layer 114A and the intermediate layer 114B are modeled together as one layer for purposes of analysis employing the methods and systems as described herein. In this example, the one or more computing systems 116 may determine one or more parameters of an optical dispersion model of the film layer 114 including both the intermediate layer 114B and high-k insulative layer 114A. However, in some other examples, each layer may be modeled separately. In this example, the one or more computing systems 116 may determine one or more parameters of an optical dispersion model of the high-k insulative layer 114A and one or more parameters of an optical dispersion model of the intermediate layer 114B film layer.

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described above. Therefore, the above description should not be interpreted as a limitation on the present invention but merely an illustration. Further, the one or more computing systems 116 may be configured to perform any other step(s) of any of the method embodiments described herein.

In another embodiment, the computer system 116 may be communicatively coupled to the spectrometer 104 or the illuminator subsystem 102 of the ellipsometer 101 in any manner known in the art. For example, the one or more computing systems 116 may be coupled to a computing system of the spectrometer 104 of the ellipsometer 101 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100. Further, the computing system 116 may be configured to receive spectral results via a storage medium (i.e., memory). For instance, the spectral results obtained using a spectrometer of an ellipsometer may be stored in a permanent or semi-permanent memory device. In this regard, the spectral results may be imported from an external system.

Moreover, the computer system 116 may send data to external systems via a transmission medium. Moreover, the computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

The embodiments of the system 100 illustrated in FIG. 1 may be further configured as described herein. In addition, the system 100 may be configured to perform any other step(s) of any of the method embodiment(s) described herein.

Figure 3:
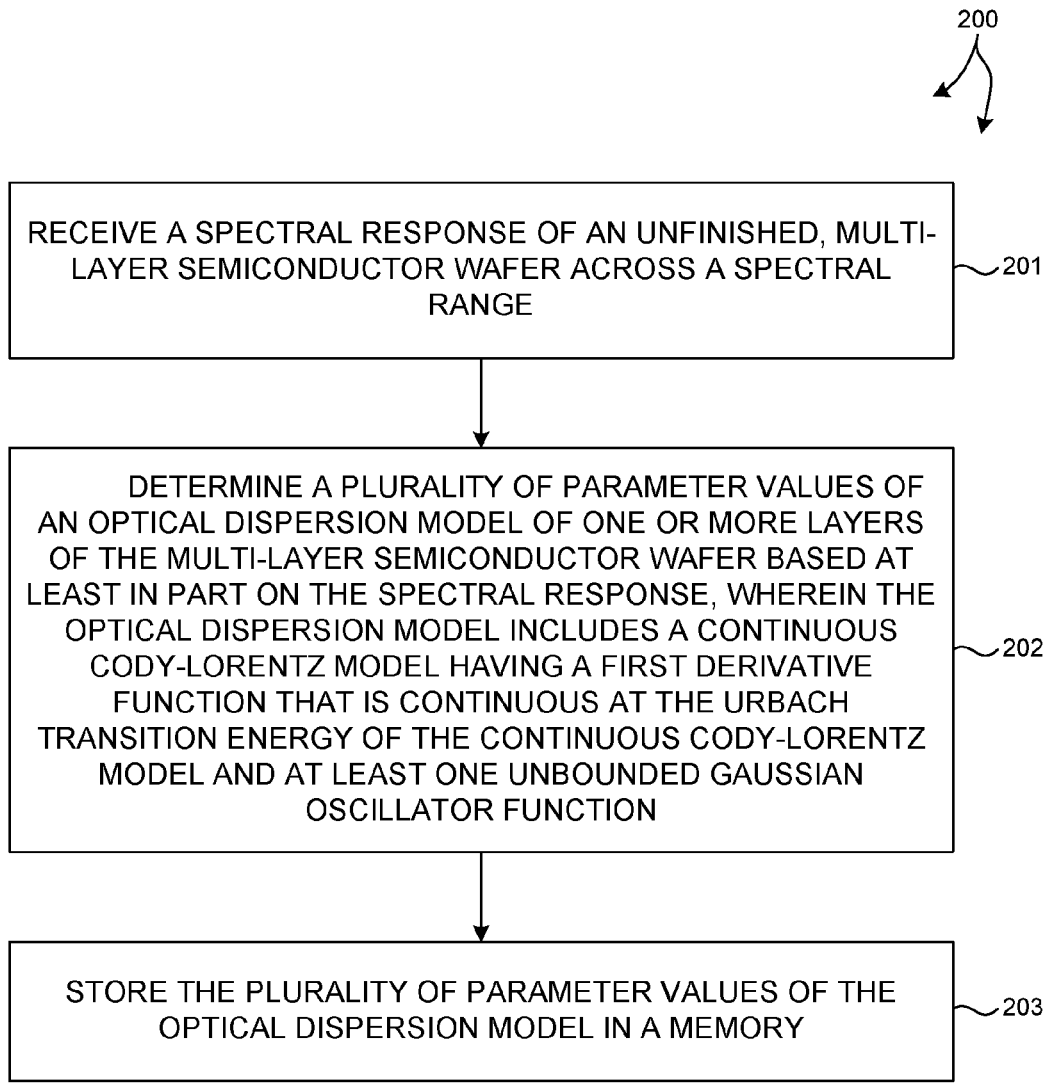
FIG. 3 is a flowchart illustrative of a method 200 of determining parameter values of a Gaussian oscillator, continuous Cody-Lorentz model from spectral response data.

FIG. 3 illustrates a process flow 200 suitable for implementation by the system 100 of the present invention. In one aspect, it is recognized that data processing steps of the process flow 200 may be carried out via a pre-programmed algorithm executed by one or more processors of computing system 116. While the following description is presented in the context of system 100, it is recognized herein that the particular structural aspects of system 100 do not represent limitations and should be interpreted as illustrative only.

In block 201, a spectral response of an unfinished, multi-layer semiconductor wafer across a broad spectral range is received by a computing system. In one example, the measurement is performed after a high-k thin film is deposited on the wafer. For example, spectra may be received from an ellipsometer 101. In another example, spectra may be received from a reflectometer (not shown). The spectral data may be acquired from each of the thin films 114 deposited on the wafer 112 utilizing the spectroscopic ellipsometer 101. For instance, the ellipsometer 101 may include an illuminator 102 and a spectrometer 104, as discussed previously herein. The spectrometer 104 may transmit results associated with a spectroscopic measurement of the thin films of the wafer to one or more computing systems 116 for analysis. In another example, the spectra for multiple thin films 114 may be acquired by importing previously obtained spectral data. In this regard, there is no requirement that the spectral acquisition and the subsequent analysis of the spectral data need be contemporaneous or performed in spatial proximity. For instance, spectral data may be stored in memory for analysis at a later time. This may be desireable, for example, for diagnostic purposes, or analysis of large sets of measurement data. In another instance, spectral results may be obtained and transmitted to an analysis computing system located at a remote location.

In block 202, a plurality of parameter values of an optical dispersion model of one or more layers of the multi-layer semiconductor wafer are determined based at least in part on the spectral response. In one example, the optical dispersion model includes at least one unbounded Gaussian oscillator function. In addition, the optical dispersion model includes a continuous Cody-Lorentz model having a first derivative function that is continuous at the Urbach transition energy of the model. In one example, the optical dispersion model includes one or more Gaussian oscillator functions to account for defect states, interface states, phonon modes, or any combination thereof. In this manner, the optical dispersion model is sensitive to one or more defects of the unfinished, multi-layer semiconductor wafer.

In general, the optical dispersion model as described herein may be configured to characterize any useful optical dispersion metric. For example, any of the real (n) and imaginary (k) components of the complex index of refraction may be characterized by the optical dispersion model. In another example, any of the real ($\in_1$) and imaginary ($\in_2$) components of the complex dielectric constant may be characterized by the optical dispersion model. In other examples, any of the square root of $\in_2$, absorption constant $\alpha = 4\pi k/\lambda$, conductivity ($\sigma$), skin depth ($\delta$), and attenuation constant $(\sigma/2)*sqrt(\mu/\in)$, where $\mu$ is the free space permeability, may be characterized by the optical dispersion model. In other examples, any combination of the aforementioned optical dispersion metrics may be characterized by the optical dispersion model. The aforementioned optical dispersion metrics are provided by way of non-limiting example. Other optical dispersion metrics or combinations of metrics may be contemplated.

In one example, the parameter values of an optical dispersion model of the real ($\in_1$) and imaginary ($\in_2$) components of the complex dielectric constant across the selected spectral range are determined utilizing a regression process. In this regard, a regression method may be applied to the measured spectral data using a selected dispersion model.

In one aspect, the selected dispersion model includes a continuous Cody-Lorentz model having continuous first derivatives and one or more Gaussian oscillator functions to describe the complex bulk band structure of high-K dielectric layer. In one example, the imaginary part of the dielectric function, $\in_2(E)$, is defined by Equation (1). The imaginary part of the dielectric function is proportional to the absorption coefficient.

$$\varepsilon_2(E) = L_f(E) + G_f + \frac{E_1}{E}\exp\left(\frac{E-E_t}{E_u}\right), 0 < E < E_t \quad (1)$$
$$= L_f(E) + G_f(E) + G_C(E)L_b(E), E \geq E_t$$

The first term in Equation (1), $L_f(E)$, represents the sum of free (unbounded) Lorentz oscillators as illustrated in equation (2).

$$L_f(E) = \sum_m \frac{A_{fm}E_{0fm}\Gamma_{fm}E}{(E_{0fm}^2 - E^2)^2 + \Gamma_{fm}^2 E^2} \quad (2)$$

$A_{fm}$, $E_{0fm}$, and $\Gamma_{fm}$ are the amplitude, frequency, and width of the m-th free Lorentz peaks, respectively, where m is any positive, integer value. As illustrated in equation (1), the model distinguishes between bounded and free (unbounded) Lorentz oscillators. Any Lorentz oscillator having a frequency larger than the band gap is assumed to be bounded, i.e., $E_{0nb} > E_g$. Any Lorentz oscillator having a frequency less than the band gap is assumed to be free, i.e., $E_{0mf} < E_g$.

The second term in Equation (1), $G_f(E)$, represents a set of the Gaussian oscillators as illustrated in equation (3).

$$G_f(E) = \sum_l A_l\left[e^{-\left(\frac{E-E_{0l}}{C_l}\right)^2} - e^{-\left(\frac{E+E_{0l}}{C_l}\right)^2}\right] \quad (3)$$

$A_l$, $E_{0l}$, and $C_l$ are the amplitude, frequency and width of the l-th Gaussian oscillators, respectively, where l is any positive, integer value. The Gaussian oscillators are free (unbounded) regardless their location with respect to the band gap. The Gaussian oscillators effectively model amorphous and glassy materials as well as phonon contribution to absorption. Further details are described by D. D. S. Meneses et al., "Structure and lattice dynamics of binary silicate glasses investigated by infrared spectroscopy," J. of Non-Crystalline Solids 352, 769-776 (2006) and S. A. MacDonald, et al., "Dispersion analysis of FTIR reflection measurements in silicate glasses," J. of Non-Crystalline Solids 275, 72-82 (2000), the subject matter of each is incorporated herein by reference in their entirety.

In the energy range, $0 < E < E_t$, equation (1) describes the Urbach tails with an exponential function where $E_t$ is the Urbach transition energy, $E_u$ is the rate of attenuation of the Urbach function, and $E_1$ is the amplitude of the Urbach function. In the energy range, $E \geq E_t$, the Cody-Lorentz function is defined as the bounded Lorentz function, $L_b(E)$, modulated by a gap function used to describe the band-edge of amorphous dielectrics. The gap function is described by equation (4), $$G_c(E) = \frac{(E-E_g)^2}{(E-E_g)^2 + E_p^2} \quad (4)$$

where $E_g$ is the band gap and $E_p$ is the transition energy. The gap function described by equation (4) modulates the sum of bounded Lorentz oscillators described by equation (5), $$L_b(E) = \sum_n \frac{A_{bn}E_{0bn}\Gamma_{bn}E}{(E_{0bn}^2 - E^2)^2 + \Gamma_{bn}^2 E^2} \quad (5)$$

where $A_{bn}$ is the amplitude of the n-th, bounded Lorentz peak describing the optical response, $E_{0bn}$ is the resonant energy of the n-th, bounded Lorentz function describing the optical response, and $\Gamma_{bn}$ is the width of the n-th, bounded Lorentz function describing the optical response, where n is any positive, integer value.

The amplitude of the Urbach function, $E_1$, is defined to enforce continuity of the dielectric function (1) at the demarcation energy, $E_t$, as described by equation (6) for the case of just one bounded, Lorentz oscillator.

$$E_1 = E_t G_C(E_t) L(E_t) \quad (6)$$

The conventional Cody-Lorentz model formulation constrains the main characteristic energies of the model such that $E_g \leq E_t < E_0$. This implies that the transition energy, $E_t$, between the Urbach tails and the gap region cannot be smaller than the band gap energy, $E_g$, and cannot be larger than the resonant energy, $E_0$, where the resonant energy corresponds approximately to the maximum of the absorption band. Moreover, the rate of attenuation of the Urbach tail is constrained to be non-negative, $E_u \geq 0$. An important limitation of the conventional Cody-Lorentz model formulation is that it has discontinuous derivatives over energy, E, and resonant energy, $E_0$ at the transition energy, $E_t$.

In a further aspect, the dispersion function defined by Equations (1)-(6) is constrained such that the constrained dispersion function has continuous derivatives over E and $E_0$ at the transition energy, $E_t$. In one example, the rate of attenuation of the Urbach function, $E_u$, is defined by equation (7), $$E_u = \frac{E_1}{\frac{\partial E_1}{\partial E_t}} = \frac{E_1}{2D} \quad (7)$$

where, $$D = \frac{E_0^4 - E_t^4}{(E_0^2 - E_t^2)^2 + \Gamma^2 E_t^2} + \frac{E_p^2}{(E_t - E_g)^2 + E_p^2} \cdot \frac{E_t}{E_t - E_g} \quad (8)$$

As a result, the continuous Cody-Lorentz model includes six fitting parameters in terms of energy, $\{E_g, E_p, A, E_0, \Gamma, E_t\}$, provided that $E_u$ is defined by Equations (7) and (8). Furthermore, as follows directly from equation (8), $E_u$ is constrained to be a non-negative value within the transition energy range $E_g \le E_t < E_0$. Therefore, the continuous Cody-Lorentz model is intrinsically well-defined and physically meaningful.

The real part of the dielectric function, $\varepsilon_1(E)$, is determined by enforcing Kramers-Kronig consistency to arrive at the following expression for $\varepsilon_1(E)$:

$$\varepsilon_1(E, b_i) = \varepsilon_1(\infty) + \frac{2}{\pi} P \int_0^\infty \frac{\xi \varepsilon_2(\xi, b_i)}{\xi^2 - E^2} d\xi \qquad (9)$$

where $\varepsilon_1(\infty)$ is the high frequency electron component of the dielectric constant, P is the principal value of the integral, and $b_i$ represents all the parameters of the model including $E_g$, $E_p$, $E_t$, $E_{0bn}$, $E_{0fm}$, $A_{bn}$, $A_{fm}$, $\Gamma_{bn}$, $\Gamma_{fm}$, $A_l$, $E_{0l}$, $C_l$, where n, m, and l run over all bounded Lorentz peaks, free Lorentz peaks and Gaussian peaks, respectively, provided that the value of $E_u$ is defined by equations (7) and (8). Equation (9) can be reformulated from its integral form to an analytical expression as follows:

$$\varepsilon_1(E) = \varepsilon_1(\infty) + I_U(E) + \sum_{n=1:8} (X_n \varphi_n) \qquad (10)$$

where $I_u(E)$ is the Urbach integral and $X_n$ and $\varphi_n$ are well-defined functions of the model parameters.

The GOCCL model described herein can be generalized to include any number of the defect levels. Also, the representation of shapes of absorption defect peaks is achieved with one or more Gaussian functions, one or more Lorentz functions, or both. Absorption defect peaks characterized by a Gaussian shape offer an improved representation of a variety of physical features of measured structures, including excitonic and chaos effects.

Figure 4:
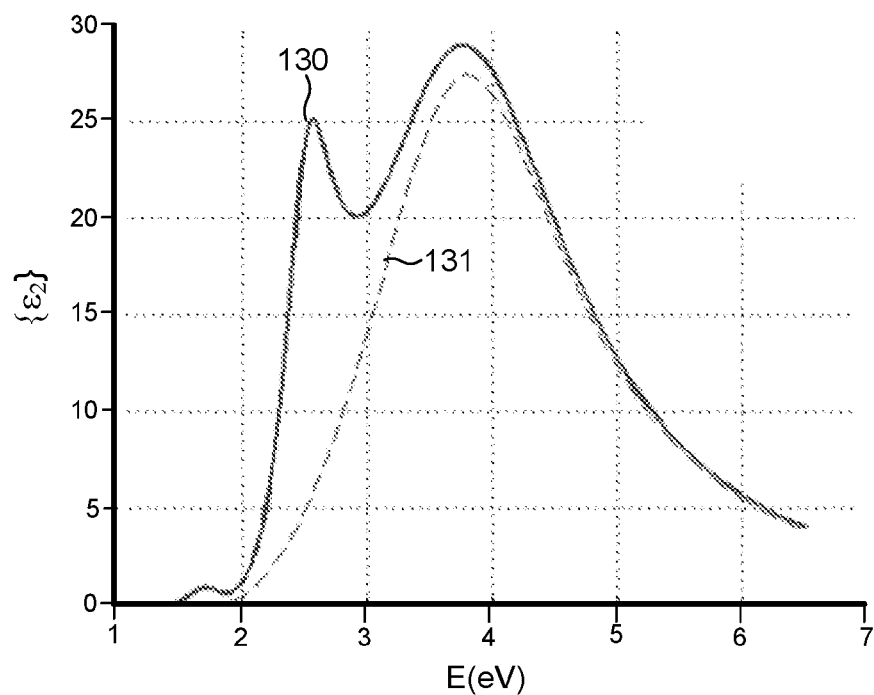
FIG. 4 is a plot illustrative of a simulation of the imaginary part of a dielectric function of a thin film sample based on the Gaussian oscillator, continuous Cody-Lorentz model described herein and a conventional Cody-Lorentz model.

FIG. 4 is a plot 130 of a simulation of the imaginary part of the dielectric function, $\varepsilon_2(E)$, modeled in accordance with the Gaussian Oscillator, Continuous-Cody-Lorentz (GOCCL) model described herein. In this example, the GOCCL model includes two bounded Lorentz oscillators and one Gaussian oscillator. In contrast, FIG. 4 also illustrates a plot 131 of a simulation of the imaginary part of the dielectric function, $\varepsilon_2(E)$, modeled in accordance with a conventional single-oscillator, Cody-Lorentz model formulation.

Figure 5:
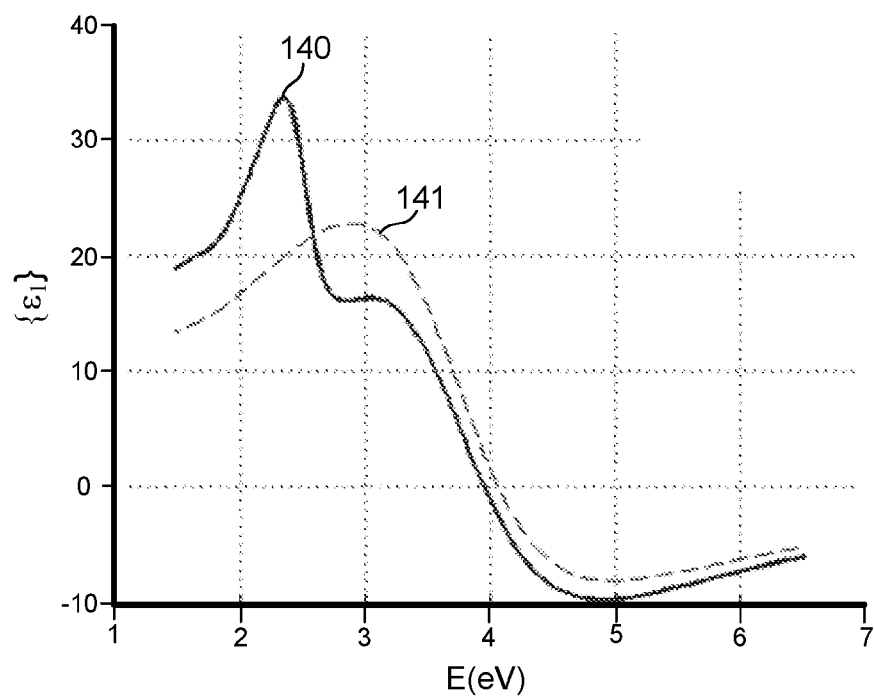
FIG. 5 is a plot illustrative of a simulation of the real part of a dielectric function of a thin film sample based on the Gaussian oscillator, continuous Cody-Lorentz model described herein and the conventional Cody-Lorentz model described with reference to FIG. 4.

FIG. 5 is a plot 140 of a simulation of the real part of the dielectric function, $\varepsilon_1(E)$, modeled in accordance with the Gaussian Oscillator, Continuous-Cody-Lorentz (GOCCL) model depicted in FIG. 4. The real part of the dielectric function is calculated using the Kramers-Kronig transformation illustrated in equation (9). In contrast, FIG. 5 also illustrates a plot 141 of a simulation of the real part of the dielectric function, $\varepsilon_1(E)$, modeled in accordance with the conventional single oscillator, Cody-Lorentz model formulation depicted in FIG. 4.

The optical function described by Equations (1)-(10) is a continuous function with continuous derivatives, and is thus, physically reasonable. In addition, maintaining Kramers-Kronig consistency between the real and imaginary parts of the optical dispersion model ensures that the functions defined by the model are physically meaningful. Reformulating the optical function enforcing Kramers-Kronig consistency (e.g., Equations (1)-(8)) into a closed form analytical expression (e.g., Equation (9)) allows for more rapid computation. In addition, the parametric derivatives of the optical function can be found in closed form. The availability of closed form expressions for the optical function and its derivatives is required to perform efficient, effective regression calculations.

In a further aspect, a band structure characteristic indicative of an electrical performance of the measured layer, or stack of layers, is determined based at least in part on the parameter values of the GOCCL model of the multi-layer semiconductor wafer. The parameters of the model, e.g., $\{E_g, E_p, E_t, E_{0bn}, E_{0fm}, A_{bn}, A_{fm}, \Gamma_{bn}, \Gamma_{fm}, A_l, E_{0l}, C_l\}$, are not just fitting parameters, but are directly related to physically measurable values. In particular, $E_g$, represents the band gap energy, $A_{bn}$, $E_{0bn}$, and $\Gamma_{bn}$, are related to band-to-band optical transitions, $A_{fm}$, represents the exciton transition strength or concentration of defects, $E_{0fm}$, represents the corresponding energies, and $\Gamma_{fm}$, are related to defect/exciton trap lifetime. Moreover, the parameters related to the l-th Gaussian oscillators, $A_l$, $E_{0l}$, and $C_l$, are related to particular phonon modes or in-gap defects contributing to the absorption coefficient. The derived optical functions represent optical features, structural features, or both, from a variety of materials of technological importance. Parameter values of the optical dispersion model are resolved based on measured data and the measurements are employed to monitor band gap as well as defects including charge trapping centers, phonon modes, or both. In addition, the parameter values can also be used to control fabrication processes.

In one example, the GOCCL model described herein can be applied to monitor band gap of high-K dielectric stacks. Moreover, the determined band gap is highly correlated to the electrical performance test results of high-K metal gate stacks. In one example, the GOCCL model described herein can be used to determine band gap estimates based on measured data that accurately predict the leakage current of semiconductor gate stacks before the semiconductor device is fully fabricated. In addition to silicon based semiconductor devices, similar results may be obtained for a variety of semiconductor devices based on Germanium Silicon and other narrow-gap semiconductors.

The aforementioned examples are provided for illustration purposes and do not limit the type of band structure characteristics that may be contemplated. Many other band structure characteristics that correlate with the electrical properties, and thus act as effective indicators of the electrical performance of a finished wafer, may be contemplated. For example, the electrical performance of the multi-layer semiconductor wafer may be expressed as any of an equivalent oxide thickness (EOT), a leakage current, a threshold voltage, and a breakdown voltage based on measured band structure characteristics.

In one embodiment, the optical dispersion model described with reference to Equations (1)-(8) has been implemented in the Film Thickness Measurement Library (FTML) of the Off-line Spectral Analysis (OLSA) stand-alone software designed to complement thin film measurement systems such as the Aleris 8510 available from KLA-Tencor Corporation, Milpitas, Calif. (USA). Measurements performed on test samples including high-K gate dielectric stacks showed high precision and reliability at high throughput. Furthermore, extracted optical functions show promise for monitoring and controlling charge trapping centers. In some examples, improved fitting of ellipsometric data with a 2-3 times improvement in throughput was observed in comparison to existing methods.

In block 203, the plurality of parameter values of the optical dispersion model determined from a fitting of measurement data to the GOCCL model are stored in a memory (e.g., a memory of carrier medium 118). The stored values may be used, for example, to perform further analysis of the specimen, or to control manufacturing process parameters.

In another further aspect, device performance is improved by controlling a process of manufacture of the semiconductor wafer based at least in part on the identified band structure characteristic. In one example, film thickness may be controlled based on band structure characteristics identified from the parameter values of the optical dispersion model illustrated in Equations (1)-(8).

Although, the GOCCL model is described with reference to modeling of high-K dielectric layers, the model can be applied to other materials. In some examples, the model can be configured to describe the band structure of a variety of nanostructures (e.g., nanowires, quantum dots and quantum wells), including any number of bands of any origin, such as excitonic states. The model can be generalized to include any number of defect levels. In another example, the model can be applied to nanostructures (e.g., quantum wells, quantum dots and nanowires) embedded in another amorphous dielectric slab or layer. In another example, the model can be applied to newly developed photoresists such as molecular resists or copolymers, high-K dielectrics such as HfO2, disordered materials, and uranium oxides (UOx).

In another further aspect, separate determinations of optical dispersion metrics and band structure characteristics associated with different layers of a wafer can be made based on the same spectral response data. For example, a wafer under measurement may include a semiconductor substrate 112, an intermediate layer 114B, a high-k insulative layer 114A, and an additional film layer (not shown). The spectral response data received from spectrometer 104 includes contributions from all of these layers. A stack layer model that captures the contributions of each of these layers can be used to separately determine band structure characteristics associated with each different physical layer or group of physical layers under analysis.

In another further aspect, the stack model includes a model of the intrinsic absorption peaks of the semiconductor substrate 112 (e.g., silicon). In one example, the intrinsic absorption peaks are accounted for in the spectral measurement of the high-k film. In this manner, the absorption peaks of the semiconductor substrate may be effectively removed from the spectral response of the high-k film. By isolating the spectral response of the high-k film from the semiconductor substrate, a more accurate determination of defects and band structure characteristics associated with the high-k film layer is achieved.

In another further aspect, band structure characteristics (e.g., band gap and defects) are used to grade wafers and microchips early in the production process based on the quality of the gate insulator. This may avoid the need to grade wafers and microchips at the end of the production process using expensive and time consuming electrical test equipment.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

A typical semiconductor process includes wafer processing by lot. As used herein a "lot" is a group of wafers (e.g., group of 25 wafers) which are processed together. Each wafer in the lot is comprised of many exposure fields from the lithography processing tools (e.g. steppers, scanners, etc.). Within each field may exist multiple die. A die is the functional unit which eventually becomes a single chip. One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for characterizing thin films of another specimen such as a reticle, which may also be commonly referred to as a mask or a photomask. Many different types of reticles are known in the art, and the terms "reticle," "mask," and "photomask" as used herein are intended to encompass all types of reticles known in the art.

Although embodiments are described herein with respect to measurement of thin films applied to wafers, it is to be understood that the methods and systems disclosed herein may be used for characterizing critical dimensions of semiconductor structures, overlay among layers of semiconductor structures, and material composition of semiconductor structures.

The embodiments described herein generally relate to methods for determining band structure characteristics of multi-layer thin films based on optical model parameter values at high throughput. For example, one embodiment relates to a computer-implemented method for determining band structure characteristics of multi-layer thin films based on optical model parameter values derived from spectroscopic ellipsometer data. However, in other examples, measurement of critical dimensions, overlay, and material composition using the techniques described herein is also contemplated. Similarly, the methods described herein are not limited in the types of metrology systems from which optical model parameter values may be derived. For example, in one embodiment, the metrology system includes a reflectometer for thin film inspection of the wafer. In general, the optical dispersion models described herein may be applied to the analysis of measurement data received from a variety of broadband and narrowband metrology tools. For example, spectroscopic ellipsometers and reflectometers, multi-angle ellipsometers and reflectometers, including any number or type of illumination sources (e.g., lamp or laser based sources emitting light in the visible, infra-red, ultra-violet, vacuum ultraviolet, deep ultraviolet spectrums) may be contemplated within the scope of this patent document.

In addition, the metrology system may be configured for inspection of patterned wafers and/or unpatterned wafers. The inspection system may be configured as a LED inspection tool, edge inspection tool, backside inspection tool, macro-inspection tool, or multi-mode inspection tool (involving data from one or more platforms simultaneously), and any other metrology or inspection tool that benefits from the determination of band structure characteristics of multi-layer thin films based on optical model parameter values at high throughput. Thus, the terms "metrology" system and "inspection" system may be used interchangeably.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A system comprising:
   an illuminator configured to provide an amount of illumination to an unfinished, multi-layer semiconductor wafer across a spectral range;
   a spectrometer configured to collect an amount of light from the unfinished, multi-layer semiconductor wafer in response to the illumination provided by the illuminator and generate an amount of data indicative of a spectral response of the unfinished, multi-layer semiconductor wafer; and
   one or more computer systems configured to:
      receive the spectral response of the unfinished, multi-layer semiconductor wafer across the spectral range;
      determine a plurality of parameter values of an optical dispersion model of one or more layers of the multi-layer semiconductor wafer based at least in part on the spectral response, wherein the optical dispersion model includes a continuous Cody-Lorentz model having a first derivative function that is continuous at the Urbach transition energy of the continuous Cody-Lorentz model and at least one unbounded Gaussian oscillator function; and
      store the plurality of parameter values of the optical dispersion model in a memory.

2. The system of claim 1, wherein the optical dispersion model is sensitive to a band gap of a layer of the unfinished, multi-layer semiconductor wafer.

3. The system of claim 1, wherein the one or more computer systems are further configured to:
   determine a band structure characteristic indicative of an electrical performance of a first layer of the multi-layer semiconductor wafer based at least in part on parameter values of the optical dispersion model of the multi-layer semiconductor wafer.

4. The system of claim 3, wherein the electrical performance of the multi-layer semiconductor wafer is any of an equivalent oxide thickness (EOT), a leakage current, a threshold voltage, and a breakdown voltage.

5. The system of claim 3, wherein the one or more computer systems are further configured to:
   control a process of manufacture of the unfinished, multi-layer semiconductor wafer based at least in part on the band structure characteristic.

6. The system of claim 1, wherein one or more layers of the multi-layer semiconductor wafer include at least one nanostructure.

7. The system of claim 6, wherein the at least one nanostructure is any of a plurality of quantum dots, a plurality of nanowires, and a plurality of quantum wells.

8. The system of claim 1, wherein a first layer of the multi-layer semiconductor wafer is an electrically insulative layer disposed above a semiconductor substrate.

9. The system of claim 8, wherein the first layer includes an intermediate layer between the semiconductor substrate and the electrically insulative layer.

10. The system of claim 1, wherein the illuminator and spectrometer are configured as any of an ellipsometer and a reflectometer.

11. A method comprising:
   receiving a spectral response of an unfinished, multi-layer semiconductor wafer across a spectral range;
   determining a plurality of parameter values of an optical dispersion model of one or more layers of the multi-layer semiconductor wafer based at least in part on the spectral response, wherein the optical dispersion model includes a continuous Cody-Lorentz model having a first derivative function that is continuous at the Urbach transition energy of the continuous Cody-Lorentz model and at least one unbounded Gaussian oscillator function; and
   storing the plurality of parameter values of the optical dispersion model in a memory.

12. The method of claim 11, wherein the optical dispersion model is sensitive to a band gap of a layer of the unfinished, multi-layer semiconductor wafer.

13. The method of claim 11, further comprising:
   determining a band structure characteristic indicative of an electrical performance of a first layer of the multi-layer semiconductor wafer based at least in part on parameter values of the optical dispersion model of the multi-layer semiconductor wafer.

14. The method of claim 13, wherein the electrical performance of the multi-layer semiconductor wafer is any of an equivalent oxide thickness (EOT), a leakage current, a threshold voltage, and a breakdown voltage.

15. The method of claim 13, further comprising:
controlling a process of manufacture of the unfinished, multi-layer semiconductor wafer based at least in part on the band structure characteristic.

16. A non-transitory, computer-readable medium, comprising:
code for causing a computer to receive a spectral response of an unfinished, multi-layer semiconductor wafer across a spectral range;
code for causing the computer to determine a plurality of parameter values of an optical dispersion model of one or more layers of the multi-layer semiconductor wafer based at least in part on the spectral response, wherein the optical dispersion model includes a continuous Cody-Lorentz model having a first derivative function that is continuous at the Urbach transition energy of the continuous Cody-Lorentz model and at least one unbounded Gaussian oscillator function; and
code for causing the computer to store the plurality of parameter values of the optical dispersion model in a memory.

17. The non-transitory, computer-readable medium of claim 16, wherein the optical dispersion model is sensitive to a band gap of a layer of the unfinished, multi-layer semiconductor wafer.

18. The non-transitory, computer-readable medium of claim 16, further comprising:
code for causing the computer to determine a band structure characteristic indicative of an electrical performance of a first layer of the multi-layer semiconductor wafer based at least in part on parameter values of the optical dispersion model of the multi-layer semiconductor wafer.

19. The non-transitory, computer-readable medium of claim 18, wherein the electrical performance of the multi-layer semiconductor wafer is any of an equivalent oxide thickness (EOT), a leakage current, a threshold voltage, and a breakdown voltage.

20. The non-transitory, computer-readable medium of claim 18, further comprising:
code for causing the computer to control a process of manufacture of the unfinished, multi-layer semiconductor wafer based at least in part on the band structure characteristic.

* * * * *